United States Patent [19]

Sircar et al.

[11] 4,134,900

[45] Jan. 16, 1979

[54] 5,6-DIHYDRO-4-OXO-4H-THIENO[2,3-b]THIOPYRAN-5-CARBOXAMIDES, AND PROCESS FOR THE PREPARATION THEREOF

[75] Inventors: Jagadish C. Sircar, Dover; Stephen J. Kesten, Morris Plains; Harold Zinnes, Rockaway, all of N.J.

[73] Assignee: Warner-Lambert Company, Morris Plains, N.J.

[21] Appl. No.: 857,337

[22] Filed: Dec. 5, 1977

Related U.S. Application Data

[62] Division of Ser. No. 749,507, Dec. 10, 1976, Pat. No. 4,092,325.

[51] Int. Cl.² .................. C07D 333/24; C07D 333/38
[52] U.S. Cl. .............................................. 260/332.2 A
[58] Field of Search ................................ 260/332.2 A

[56] References Cited

U.S. PATENT DOCUMENTS 3,828,055  8/1974  Zinnes et al. ................ 260/294.8 C

OTHER PUBLICATIONS

Cagniant et al., Bull. Soc. Chim. Fr. 2172 (1966).

*Primary Examiner*—Gerald A. Schwartz
*Attorney, Agent, or Firm*—Albert H. Graddis; Frank S. Chow; Anne M. Kelly

[57] ABSTRACT

This invention relates to 5,6-dihydro-4-oxo-4H-theino[2,3-b]thiopyran-5-carboxamides of the Formula I:

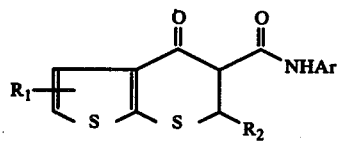

wherein $R_1$ is hydrogen, halogen or lower alkyl; $R_2$ is hydrogen, lower alkyl or aryl; and Ar is aryl or heterocyclic; their pharmaceutically acceptable salts and to processes for their preparation. The compounds of this invention exhibit antibacterial, antifungal and antiallergy activity.

2 Claims, No Drawings

5,6-DIHYDRO-4-OXO-4H-THIENO[2,3-B]THIOPYRAN-5-CARBOXAMIDES, AND PROCESS FOR THE PREPARATION THEREOF

This is a division of application Ser. No. 749,507 filed Dec. 10, 1976 now U.S. Pat. No. 4,092,325.

DESCRIPTION OF THE INVENTION

This relates to novel 5,6-dihydro-4-oxo-4H-thieno[2,3-b]thiopyran-5-carboxamides of the Formula I:

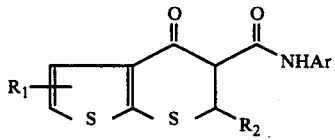

wherein $R_1$ is hydrogen, halogen or lower alkyl; $R_2$ is hydrogen, lower alkyl or aryl; Ar is aryl or heterocyclic; and their pharmaceutically acceptable salts.

This invention also includes within its scope novel processes for preparing the above compounds as well as intermediates employed in their synthesis.

The compounds of the Formula I are prepared by the following sequence: Reaction of a compound of the Formula II:

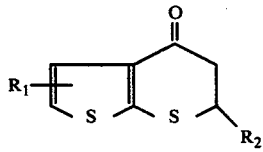

wherein $R_1$ and $R_2$ are as defined above in Formula I, with a sodium alkoxide and a (dialkyl)oxalate to give a compound of the Formula III:

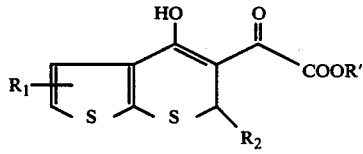

wherein $R_1$ and $R_2$ are as defined above in Formula II and R' is lower alkyl. In aforementioned reaction, the alkyl group in the sodium alkoxide may vary but must be the same as the alkyl groups in the oxalate diester. Typically, sodium methoxide and dimethyl oxalate are used.

Compound III is then subjected to decarbonylation at at 170° C. to 180° C. in the presence of powdered glass, to obtain a compound of the Formula IV:

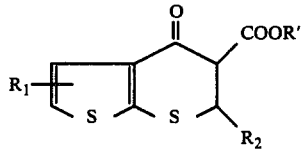

wherein $R_1$, $R_2$ and R' are as defined above in Formula III.

Compound IV is reacted with an appropriate amine in a suitable high boiling solvent such as xylene to obtain the desired Compound I. Amines having the formula:

$$NH_2-Ar$$

are suitable for use in this last mentioned reaction, wherein Ar is a monocyclic aromatic hydrocarbon; a substituted monocyclic aromatic hydrocarbon wherein the substituent may be halogen, lower alkoxy, trifluoromethyl and the like; a monocyclic heterocycle; or a substituted monocyclic heterocycle wherein the substituent may be halogen, lower alkoxy, trifluoromethyl and the like. Typical amines include aniline, amino-substituted pyridine, amino-substituted isoxazole, amino-substituted thiazole and the like.

The starting material II (5,6-dihydro-4H-thieno[2,3-b]-thiopyran-4-one, $R_1 = R_2 = H$), is prepared according to the procedure of P. Cagniant and Mme. Densie Cagniant, *Bull. Soc. Chim. Fr.*, 2172 (1966) or by a chemically known, obvious variation of this procedure.

The compounds of this invention exhibit antibacterial, antifungal and antiallergy activity. Compounds of the Formula I show antibacterial and antifungal activity. For example, 5,6-dihydro-N-(5-methyl-3-isoxazolyl)-4-oxo-4H-thieno[2,3-b]-thiopyran-5-carboxamide is active against fungi such as *C. albicans* and *T. mentagrophytes*, showing minimum inhibitory concentrations in the range of 125 to 1000 mcg/ml, when evaluated in the in vitro tube dilution procedure described in U.S. Pat. No. 3,651,216. Thus, these compounds are useful in the treatment of fungal infections. The novel antibacterial, antifungal substances of this invention can be formulated with inert excipients into various dosage forms for oral, parenteral and topical adminstration by methods well-known to those skilled in the pharmacist's art. Tablets, capsules, powders, solutions, suspensions, ointments, gels and creams are included among the suitable dosage forms.

Compounds of the invention having the Formula III are active in prevention of allergic and asthmatic reactions in rats at dose levels of 25 to 100 mg/kg. Thus methyl 4-4-hydroxy-α-oxo-6H-thieno[2,3-b]thiopyran-5-acetate shows a 49% inhibition of the allergic response at 25 mg/kg when tested intraperitoneally in the passive cutaneous anaphalaxis (PCA) screen, which is a modification of procedures described by I. Mota, *Life Sciences*, 7:465 (1963) and Z. Ovary and O. Bier, *Proc. Soc. Exptl. Biol. Med.*, 81:585 (1952). Consequently, they may be useful in the treatment of asthma, hay fever and other allergic conditions.

The compounds of this invention having Formula III can be administered orally or parenterally as aqueous suspensions or as aqueous solutions of their alkali metal salts.

Compounds of the invention having the Formula IV are useful as intermediates to sythesize 4-hydroxy-6H-thieno [2,3-]thiopyran-5-carboxamides 7,7-dioxide which show antiinflammatory activity. The preparation and the activity of 4-hydroxy-6H-thieno[2,3-b]thiopyran-5-carboxamides 7,7-dioxides are the subject of copending U.S. application Ser. No. 749,491 filed Dec. 10, 1976, now U.S. Pat. No. 4,082,757 by Jagadish C. Sircar, Stephen J. Kesten and Harold Zinnes, entitled "Amides of 4-Hydroxy-6H-Thieno[2,3-b]Thiopyran-5-Carboxylic Acid-7,7-Dioxide and Process for the Preparation Thereof," (2100.1239).

The following definitions apply to all of the compounds, intermediates and processes of this invention:

lower alkyl is meant to include 1 to 7 carbon, preferably 1 to 4 carbon, straight or branched alkyl chains; aforementioned definition of lower alkyl applies of the alkyl portion of the term lower alkoxy and to the alkyl portion of the term alkoxide; halogen is meant to include chlorine, bromine and iodine; aryl is meant to include monocyclic aromatic hydrocarbons; substituted monocyclic aromatic hydrocarbons wherein the substituent may be halogen, lower alkoxy, trifluoromethyl and the like; monocyclic heterocycles; and substituted monocyclic heterocycles wherein the substituent may be halogen, lower alkoxy, trifluoromethyl and the like.

In order to further illustrate this invention, the following examples are provided:

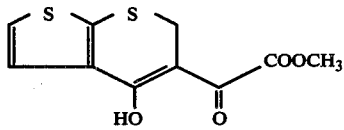

Methyl 4-hydroxy-α-oxo-6H-thieno[2,3-b]-thiopyran-5-acetate.

A mixture of sodium methoxide (21.6 g, 0.4 mole) and dimethyloxalate (47.2 g, 0.4 mole) in benzene (300 ml) is refluxed for 5 min. in order to dissolve most of the solid. To the cooled solution is added a solution of 5,6-dihydro-4H-thieno[2,3-b]-thiopyran-4-one (34 g, 0.2 mole) in benzene (300 ml) and the mixture is stirred for 3 hrs. to give a yellow suspension. The mixture is poured into ice-water mixture (1750 ml). After separating the aqueous layer from the benzene layer, the benzene layer is extracted with 1(N) NaOH solution (250 ml), and the combined aqueous solution is washed once with ether (100 ml) and acidified with (N) HCl. The yellow crystalline glyoxalate is filtered off and dried over $P_2O_5$ to give 45.8 g (91%) of the desired product; m.p. 53–56° C.

IR ($CHCl_3$) 3120–3040 (b, OH), 1735 (C=O), 1605 (C=C—C=O) $cm^{-1}$.

NMR ($CDCl_3$) δ 10.6 (s, 1, OH, exchangeable); 7.35 (d, 1, $C_2$); 7.05 (d, 1, $C_3$); 4.4 (s, 2, $C_6$); 3.9 (s, 3, $OCH_3$). $\lambda_{max}^{EtOH}$ 320 (5,600), 238 (10,800) mµ

Anal. Calcd. for $C_{10}H_8O_4S_2$: C, 46.86; H, 3.15; S, 25.02. Found: C, 46.92; H, 3.23; S, 24.58, 24.64.

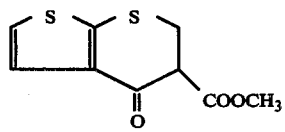

Methyl 5,6-dihydro-4-oxo-4H-thieno[2,3-b]thiopyran-5-carboxylate

A mixture of methyl 4-hydroxy-α-oxo-6H-thieno[2,3-b]-thiopyran-5-acetate (71 g) and powdered glass (71 g) is heated at 180° C. for 25 min. when a vigorous evolution of CO takes place. After cooling, the dark product is dissolved in methylene chloride and filtered from the glass, and the filtrate evaporated to dryness. The dark brown solid residue is dissolved in dry ether (2500 ml) and filtered through alumina column (3 × 13 $cm^2$). The column is washed with additional amount of dry ether (250 ml) and the total ethereal solution is slowly concentrated until the crystals starts to form. The crystals are recovered, triturated with ether and filtered to give white solid (38.2 g, 60%), m.p. 94–97° C.

IR ($CHCl_3$) 1742 (C=O), 1673 (C=O) $cm^{-1}$.

NMR ($CDCl_3$) δ 7.5 (d, 1, $C_2$), 7.0 (d, 1, $C_3$), 3.65 (m, 6, $OCH_3$, $C_5$ and $C_6$). $\lambda_{max}^{EtOH}$ 332 (4,000), 261 (9,000), 240 (18,000).

Anal. Calcd. for $C_9H_8O_3S_2$: C, 47.35; H, 3.53; S, 28.09. Found: C, 47.25; H, 3.53; S, 27.96, 28.05.

EXAMPLE 3

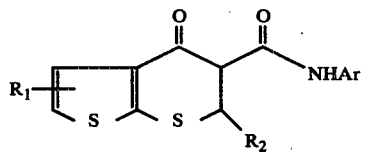

Amides of 5,6-dihydro-4-oxo-4H-thieno[2,3-b]thiopyran-5-carboxylic acid

General Procedure: A mixture of methyl 5,6-dihydro-4-oxo-4H-thieno[2,3-b]-thiopyran-5-carboxylate (5.7 g, 0.025 mole), an appropriate amine (0.0375 moles) and xylene (180 ml) is refluxed for 2.5 to 3 hrs. in a Soxhlet apparatus, the thimble of which contains 20 g of Linde type 4A molecular sieve. The mixture is cooled and the resulting crystalline product is collected and recrystallized.

EXAMPLE 4

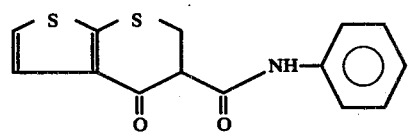

5,6-Dihydro-4-oxo-N-phenyl-4H-thieno[2,3-b]-thiopyran-5-carboxamide

A mixture of methyl 5,6-dihydro-4-oxo-4H-thieno[2,3-b]-thiopyran-5-carboxylate (5.7 g, 0.025 mole), aniline (3.5 g, 0.0375 mole) and xylene (180 ml) is refluxed for 2.5 hrs. in a Soxhlet apparatus, the thimble of which contains 20 g of Linde type 4A molecular sieve. The mixture is cooled in an ice bath, and the resulting crystalline precipitate (m.p. 155–158° C.) is collected, dried and recrystallized from methylene chloride and isopropyl ether to give 6.5 g (90%) of off-white crystalline material, m.p. 155–158° C.

IR ($CHCl_3$) 3300 (broad, NH), 1690 (C=O), 1648 (C=O), 1603 (CONH) $cm^{-1}$.

NMR ($CDCl_3$) δ 9.4 (b, 1, NH), 7.6–6.9 (m, 7, aromatic), 3.65 (m, 3, $C_5$, $C_6$). $\lambda_{max}^{EtOH}$ 330 (4,000), 242 (32,400) mµ

Anal. Calcd. for $C_{14}H_{11}NO_2S_2$: C, 58.11; H, 3.83; N, 4.84; S, 22.16. Found: C, 58.34; H, 4.01; N, 4.88; S, 22.41, 22.38.

EXAMPLE 5

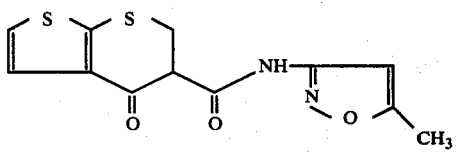

5,6-Dihydro-N-(5-methyl-3-isoxazolyl)-4-oxo-4H-thieno[2,3-b]-thiopyran-5-carboxamide This product is obtained by using 3-amino-5-methyl-isoxazole, following the procedure of Example 3. It is recrystallized from methylene chloride and isopropylether mixture. Yield 5.9 g (80%), m.p. 143–146° C.

IR (CHCl$_3$) 3400–3200 (b, NH); 1705 (C=O); 1655 (C=O); 1625 (CONH) cm$^{-1}$.

NMR (CDCl$_3$) δ 10.1 (b, 1, NH); 7.5 (d, 1, C$_2$); 7.05 (d, 1, C$_3$); 6.67 (s, 1H, C$_4'$); 3.8 (m, 3, C$_5$, C$_6$); 2.4 (s, 3, C$_5'$—CH$_3$). $\lambda_{max}^{EtOH}$ 238 (27,200) mμ.

Anal. Calcd. for C$_{12}$H$_{10}$N$_2$O$_3$S$_2$: C, 48.97; H, 3.42; N, 9.52; S, 21.79. Found: C, 48.88; H, 3.48; N, 9.56; S, 21.66, 21.73.

EXAMPLE 6

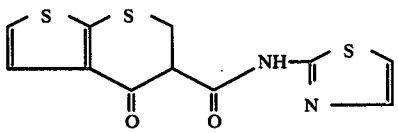

5,6-Dihydro-4-oxo-N-(2-thiazolyl)-4H-thieno[2,3-b]-thiopyran-5-carboxamide

This product is obtained by using 2-aminothiazole, following the procedure of Example 3. It is recrystallized from methanol. Yield 6.0 g (81%), m.p, 201–203° C.

IR (Nujol) 3200–3120 (broad, NH); 1665 (C=O); 1580 (CONH) cm$^{-1}$.

NMR (DMSO) δ 12.35 (b, 1, NH); 7.4 (m, 4, aromatic); 4.0 (m, 3H, c$_5$,C$_6$—). $\lambda_{max}^{EtOH}$ 266 (16,000); 240 (18,000) mμ

Anal. Calcd. for C$_{11}$H$_8$N$_2$O$_2$S$_3$: C, 44.58; H, 2.72; N, 9.45; S, 32.45. Found: C, 44.52; H, 2.77; N, 9.36; S, 32.56, 32.74.

We claim:
1. A compound of the Formula III:

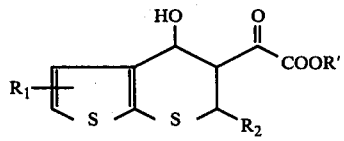

wherein R$_1$ is hydrogen, halogen or lower alkyl; R$_2$ is hydrogen, lower alkyl or aryl; and R' is lower alkyl.

2. A compound according to claim 1 which is methyl 4-hydroxy-α-oxo-6H-thieno[2,3-b]-thiopyran-5-acetate.

* * * * *

UNITED STATES PATENT OFFICE
CERTIFICATE OF CORRECTION

Patent No. 4,134,900          Dated January 16, 1979

Inventor(s) Jagadish C. Sircar, Stephen J. Kesten and Harold Zinnes

It is certified that error appears in the above-identified patent and that said Letters Patent are hereby corrected as shown below:

Column 3, line 15, insert ---Example 1---.

Column 3, line 47, insert ---Example 2---.

Signed and Sealed this

Twenty-fifth Day of September 1979

[SEAL]

Attest:

Attesting Officer

LUTRELLE F. PARKER

Acting Commissioner of Patents and Trademarks